US007893323B2

(12) United States Patent
Reynolds

(10) Patent No.: US 7,893,323 B2
(45) Date of Patent: *Feb. 22, 2011

(54) **TRANSFORMATION OF *ALLIUM SP.* WITH AGROBACTERIUM USING EMBRYOGENIC CALLUS CULTURES**

(75) Inventor: John Reynolds, Davis, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/723,129

(22) Filed: Mar. 12, 2010

(65) Prior Publication Data

US 2010/0180353 A1    Jul. 15, 2010

Related U.S. Application Data

(63) Continuation of application No. 11/446,514, filed on Jun. 5, 2006, now Pat. No. 7,714,191, which is a continuation of application No. 10/009,389, filed as application No. PCT/US00/12463 on May 5, 2000, now Pat. No. 7,067,719.

(60) Provisional application No. 60/132,617, filed on May 5, 1999.

(51) Int. Cl.
| *C12N 15/84* | (2006.01) |
| *A01H 5/00* | (2006.01) |
| *A01H 5/10* | (2006.01) |
| *A01H 4/00* | (2006.01) |

(52) U.S. Cl. ........................ 800/294; 800/269; 800/300; 435/430.1

(58) Field of Classification Search ........................ None
See application file for complete search history.

(56) References Cited

U.S. PATENT DOCUMENTS

| 5,424,412 | A | 6/1995 | Brown et al. |
| 5,591,616 | A | 1/1997 | Hiei et al. |
| 5,767,377 | A | 6/1998 | Nakajima et al. |
| 5,859,347 | A | 1/1999 | Brown et al. |
| 6,048,730 | A | 4/2000 | Waldron |
| 6,583,335 | B1 | 6/2003 | Peffley et al. |

FOREIGN PATENT DOCUMENTS

| JP | 92-060496/08 | 1/1992 |
| WO | 92/06205 | 4/1992 |
| WO | 97/42333 | 11/1997 |
| WO | 98/37212 | 8/1998 |
| WO | 98/44136 | 10/1998 |
| WO | 99/10512 | 3/1999 |
| WO | 00/44919 | 8/2000 |
| WO | 00/58484 | 10/2000 |

OTHER PUBLICATIONS

Lu et al. HortScience 22(5) and Section 2: 1131 (Oct. 1987).*
Shahin et al. HortScience 21(2): 294-295 (Apr. 1986).*
van der Valk et al. Plant Cell, Tissue and Organ Culture 30(3): 181-191 (1992).*
Peffley et al. Theoretical and Applied Genetics 71(2): 176-184 (Dec. 1985).*
Cryder et al. Theoretical and Applied Genetics 82(3): 337-345 (Sep. 1991).*
Dommisse et al., "Onion is a Monocotyledonous Host for *Agrobacterium*," *Plant Science* 69:249-257 (1990).
Dong et al., "Agrobacterium-mediated transformation of Javanica rice," *Molecular Breeding*, 2:267-276 (1996).
Eady et al., "Towards the transformation of onions (*Allium cepa*)," *New Zealand Journal of Crop and Horticultural Science*, 23(3):239-250 (1995).
Eady et al., "Transient expression of *uidA* constructs in in vitro onion (*Allium cepa* L.) cultures following particle bonbardment and *Agrobacterium* -mediated DNA delivery," *Plant Cell Reports*, 15:958-962 (1996).
Eady, "Transformation of Onion (*Allium cepa*L.)," *1998 Proceedings National Research Conference*, Sacramento, CA USA Dec. 10-12, 1998.
Eady et al., "A comparison of four selective agents to use with *Allium cepa* immature embryos and immature embryo-derived cultures," *Plant Cell Reports*, 18:117-121 (1998).
European Search Report for EP 00 93 2149 dated Apr. 22, 2002.
Examiner's Report in AU 49918/00 (Dec. 12, 2003)—Australian equivalent of the above-identified application.
Hansen et al, "Recent advances in the transformation of plants,". *Trends in Plant Science* 4:226-231 (1999).
International Search Report from PCT/US00/12463 dated Aug. 9, 2000.
Klein et al., "High-velocity microprojectiles for delivering nucleic acids into living cells," *Nature* 327:70-73 (1987).
Narasimhulu et al., "Early transcription of Agrobacterium T-DNA genes in tobacco and maize," *The Plant Cell* 8:873-874 (1996).
Official Communication in EP 00 932149.8-1212 (Feb. 3, 2003)—European equivalent of the above-identified application (2003).
Official Communication in EP 00 932149.8-1212 (Jan. 16, 2004)—European equivalent of the above-identified application (2004).
Potrykus, "Gene Transfer to Cereals: An Assessment," *Biotechnology* 8(6):535-542 (1990).
Hou, "Morphological and Molecular Tracking of *Allium fistulosum* L. Introgressed into *A. cepa* L.," *A Dissertation in Agronomy*, submitted to Texas Tech University (Aug. 1998).
Keller et al., "Interspecific Crosses of Onion with Distant *Allium* Species and Characterization of the Presumed Hybrids by Means of Flow Cytometry, Karyotype Analysis and Genomic in situ Hybridization," *Theor. Appl. Genet.*, 92:417-424 (1996).
Song et al., "Chromosome Doubling of *Allium fistulosum* × *A. cepa* Interspecific F₁ Hybrids Through Colchicine Treatment of Regenerating Callus," *Euphytica*, 93:257-262 (1997).

* cited by examiner

*Primary Examiner*—David T Fox
(74) *Attorney, Agent, or Firm*—Thomas P. McBride; Matthew L. Madsen; Arnold & Porter LLP

(57)    ABSTRACT

The present invention relates to a method for transforming *Allium* species with a heterologous gene using *Agrobacterium*.

27 Claims, No Drawings

TRANSFORMATION OF *ALLIUM SP.* WITH AGROBACTERIUM USING EMBRYOGENIC CALLUS CULTURES

This application is a continuation application of U.S. application Ser. No. 11/446,514, filed Jun. 5, 2006, now U.S. Pat. No. 7,714,191, which is a continuation of U.S. application Ser. No. 10/009,389, filed Jul. 20, 2002, now U.S. Pat. No. 7,067,719 issued Jun. 27, 2006, which was a national phase application of PCT/US00/12463, filed May 5, 2000, which claims priority under 35 U.S.C. §119(e) to Provisional Patent Application No. 60/132,617, filed May 5, 1999, now expired, all of which are expressly incorporated herein in their entirety by reference.

TECHNICAL FIELD OF THE INVENTION

The present invention relates to a method for transforming *Allium* species with a heterologous gene using *Agrobacterium*.

BACKGROUND OF THE INVENTION

Transformation in onion has eluded the scientific community. Initial work on the crop centered around use of biolistics as a means of transforming vegetable monocots (Eady, C. C., Weld, R. J. & Lister, C. E. Transformation of onion, *Allium cepa* L., *Proc. Nat. Onion Research Conference*, Sacramento, Calif. USA, Dec. 10-12, 1998). No convincing reports were published showing success using this approach. Recent success was reported in transformation of rice, wheat and corn, using *Agrobacterium* based approaches (U.S. Pat. No. 5,591,616). These reports lead to use of *Agrobacterium* for transformation in monocot vegetables. Recently, Eady (Eady, C. C., Weld, R. J. & Lister, C. E. Transformation of onion, *Allium cepa* L, *Proc. Nat. Onion Research Conference*, Sacramento, Calif. USA, Dec. 10-12, 1998) at Crop and Food, NZ, reported on successful transformation of onion using *Agrobacterium* with a kanamycin selectable marker and a Green Florescent Protein (GFP) scoreable marker.

SUMMARY OF THE INVENTION

In one embodiment, the present invention relates to a method for transforming an *Allium* species, such as *Allium cepa* or *Allium fistulosum*, with a heterologous gene. Specifically, the method involves contacting embryogenic callus material from an *Allium* species with a bacterium belong to the genus *Agrobacterium* which contains a heterologous gene. The embryogenic callus material is preferably derived from immature embryos or flower buds from an *Allium* species. Preferably, the *Agrobacterium* is *Agrobacterium rhizogenes* or *Agrobacterium tumefaciens* and contains a Ti or Ri plasmid. The heterologous gene can be the EPSPS or modified EPSPS gene.

In another embodiment, the present invention further relates to a method for transforming an *Allium* species with a heterologous gene. The first step of the method involves culturing immature embryos or flower buds from an *Allium* species such as *Allium cepa* or *Allium fistulosum* on an initiation medium for a period of from about 2 to about 6 months until embryogenic callus material forms on the embryos or flower buds. Preferably, the immature embryo or flower buds are cultured on the initiation medium in the dark and at a temperature of from about 25° C. to about 30° C. The next step of the method involves transferring the embryogenic callus material to a coculture medium and contacting the embryogenic callus material with a suspension of *Agrobacterium rhizogenes* or *Agrobacterium* tumefaciens containing a heterologous gene. The next step involves incubating the embryogenic callus with *Agrobacterium rhizogenes* or *Agrobacterium tumefaciens* for a period of from about 2 to about 4 days. The next step involves removing the *Agrobacterium rhizogenes* or *Agrobacterium tumefaciens* from the transformed embryogenic callus material. The final step involves regenerating the transformed embroygenic callus material into transformed *Allium* plants containing the heterologous gene.

Finally, the present invention relates to an *Allium* species transformed by either of the hereinbefore described methods and progeny thereof.

DETAILED DESCRIPTION OF THE INVENTION

The present invention relates to a method for transforming onion with a heterologous gene using *Agrobacterium* mediated transformation. Any type of onion can be transformed using the method of the present invention, such as, but not limited to *Allium cepa* and *Allium fistulosum*. As used herein, the term "heterologous" when used to describe a gene refers to a gene that originates from a foreign species, or, if from the same species, is substantially modified from its original form. For example, a promoter operably linked to a heterologous structural gene is from a species different from that from which the structural gene was derived, or, if from the same species, one or both are substantially modified from their original form.

The method of the present invention employs nodular embroygenic callus material. This embroygenic callus material is preferably derived from immature embryos or from flower buds using techniques which are well known in the art. For example, immature embryos can be obtained from up to fourteen (14) day old post-pollinated flowers. Immature flower buds can be obtained from unopened umbels from an onion.

Once the immature embryos or flower buds are obtained, they are placed on a callus initiation medium such as the initiation medium described in Table A as media number one (#1) and kept under appropriate environmental conditions, specifically, in the dark and at a temperature between from about 25° C. to about 30° C., to allow the formation of callus. Other initiation media which induce the formation of callus which are well known in the art, can also be used. For example, any salt formulation media, such as but not limited to, Murshige and Skoog (MS) (Murashige T., Skoog F. (1962) *Physilogia Plantarum* 15:473-497), B-5 (Gamborg, O. L., R. A. Miller, and K. Ojima (1968) "Nutrient requirements of suspension cultures of soybean root cells" *Exp. Cell Res.* 50: 148-151), Heller (Heller, R. (1953) "Recherches sur la nutrition minerale des tissus vegetaux cultivers in vitro." *Ann. Sci. Natl. Biol. Veg.* 14: 1 223), White (White. P. R. "Nutrient deficiency studies and an improved inorganic nutrient medium for cultivation of excised tomato roots." *Growth* 7: 53 (1943), which contain a high concentration of auxins (such as indole acetic acid (IAA)), 2,4-diclorophenoxy acetic acid, picloram, indole butyric acid (IBA) as well as a carbon source (such as glucose, sucrose, etc) can be used.

After about two (2) to six (6) months, a nodular embryogenic callus forms on the embryos or flowers. The callus is maintained by subculturing every four (4) weeks, keeping the culture in the dark at a temperature between about 25° C. to about 30° C. During this period, any tissue which is not nodular embryogenic callus is removed from the culture. Specifically, the removal of brown or smooth textured tissue and of tissue with anthocyanin or sticky exudates faciliates the development of the nodular embryogenic callus. The nodular embryogenic callus is the material suitable for transformation with *Agrobacterium*.

For regeneration, the nodular embryogenic callus is transferred to a regeneration medium such as the regeneration medium provided for in Table A as media number two (#2) and is placed under Cool White fluorescent light for about fourteen (14) to about eighteen (18) hours per day at a temperature between about 25° C. to about 30° C. Other regeneration media which are well known in the art can also be used. For example, any salt formulation medium, such as, but not limited to, Murshige and Skoog (MS), B-5, Heller, White, which contains low levels of cytokinins (such as benzylaminopurine (BA), kinetin, 6-dimethyallyaminopurine (2IP) and a carbon source (such as glucose, sucrose, etc.) can also be used.

Any desired heterologous or target gene can be introduced into *Allium* sp. using the method of the present invention. The heterologous gene used in the method of the present invention encodes for the expression of a protein, such as the 5-enolpyruvyl-3-phosphate synthase enzyme, which conveys resistance to the glyphosate herbicide. The desired heterologous gene to be inserted into onion can be isolated using molecular biology techniques which are well known in the art or can be produced synthetically using molecular biology techniques which are also well known in the art.

As discussed in the previous paragraph, an example of a heterologous gene that can be used in the method of the present invention is a gene which encodes for the 5-enolpyruvyl-3-phosphate synthase enzyme, which conveys resistance to the glyphosate herbicide. As is well known in the art, glyphosate inhibits the shikimic acid pathway which leads to the biosynthesis of aromatic compounds including amino acids, plant hormones and vitamins. Specifically, glyphosate curbs the conversion of phosphoenolpyruvic acid and 3-phosphoshikimic acid to 5-enolpyruvyl-3-phosphoshikimic acid by inhibiting the enzyme 5-enolpyruvyl-3-phosphate synthase (hereinafter referred to as "EPSPS" or "EPSP synthase"). It is well known that glyphosate-tolerant plants can be produced by inserting into the genome of the plant the capacity to produce a higher level of EPSP synthase in the chloroplast of the cell which enzyme is preferably glyphosate-tolerant.

Many EPSP synthase genes and the use of these genes to transform plants to make plants which are tolerant to glyphosate herbicides are well known in the art. For example, the nucleotide sequence for the mutant *E. coli* EPSP synthase aroA gene was determined by the method of Sanger, et al. (*Proc. Natl. Acad. Sci. USA* 74:5463) and the corresponding amino acid sequence for the encoded EPSP synthase deduced therefrom. U.S. Pat. No. 4,769,061 discloses a mutated aroA gene which expresses 5-enolpyruvyl-3-phosphoshikimate synthase (EC: 2.5.1.19) (ES-3-P synthase) and methods for making plants which express this mutated gene and which exhibited enhanced resistance to glyphosate herbicides. U.S. Pat. No. 4,940,835 discloses a cloning or expression vector comprising a gene which encodes EPSPS polypeptide which, when expressed in a plant cell contains a chloroplast transit peptide which allows the polypeptide, or an enzymatically active portion thereof, to be transported from the cytoplasm of the plant cell into a chloroplast in the plant cell, and confers a substantial degree of glyphosate resistance upon the plant cell and plants regenerated therefrom. U.S. Pat. No. 5,188,642 discloses how to use the vector described in U.S. Pat. No. 4,940,835 to selectively control weeds in a field. U.S. Pat. Nos. 5,145,783, 4,791,908 and 5,312,910 describe plant genes, methods for producing said genes and vectors containing these genes which encode a glyphosate-tolerant EPSP synthase where the EPSP synthase has an alanine residue substituted for a glycine residue in a conserved sequence found between positions 80 and 120 in the mature wild-type EPSP synthase. U.S. Pat. Nos. 5,627,061 and 5,310,667 discloses plant genes encoding EPSP synthases and methods for preparing said genes which are prepared by substituting an alanine residue for a glycine residue in a first conserved sequence found between positions 80 and 120, and either an aspartic acid residue or asparagine residue for a glycine residue in a second conserved sequence found between positions 120 and 160 in the mature wild type EPSP synthase. U.S. Pat. Nos. 5,633,435 and 5,804,425 disclose a modified EPSPS gene from *Agrobacterium* sp. strain CP4. U.S. Pat. No. 5,866,775 discloses plant genes which encode a glyphosate-tolerant EPSP synthase where the EPSP synthase has an alanine residue substituted for a glycine residue in a conserved sequence found between positions 80 and 120 and a threonine residue for an alanine residue in a second conserved sequence found between positions 170 and 210 in the mature wild-type EPSP synthase. Additional EPSP synthase genes are disclosed in Padgette et al., *Herbicide Resistant Crops*, Lewis Publisher pages 53-85 (1996). Thereupon, any of the hereinbefore described EPSPS genes can be used in the method of the present invention.

The heterologous gene to be expressed in onion can be used to construct an expression cassette which will be introduced into onion. The construction and composition of expression cassettes is well known in the art. Specifically, the elements of the expression cassette are the heterologous gene, a promoter and a termination DNA segment. The heterologous gene is operatively linked to a promoter DNA segments which controls the expression of the heterologous gene. As used herein, the term "operatively linked"includes reference to a functional linkage between a promoter and the heterologous gene, wherein the promoter sequence initiates and mediates transcription of the DNA sequence corresponding to the heterologous gene. Generally, operably linked means that the nucleic acid sequences being linked are contigous and, where necessary to joint two protein coding regions, contagious and in the same reading frame. This promoter is not repressed by a product of normal onion metabolism, and can be a constitutive promoter such as the CaMV 35S, octopine synthase promoter (P-Ocs) and nopaline synthase promoter (P-Nos) promoters, or organ-enhanced promoters that cause expression in one or more limited organs of the transformed onion.

The final element in the expression cassette is a termination DNA segment that is operatively linked to the 3' end of the heterologous gene. Several termination segments useful in plants are well known in the art and can be used herein. One exemplary segment is the 3' non-translated region of the nopaline synthase gene (Nos-T). Another is the 3'-non-translated region of the pea rbcS-E9 gene.

In addition, the expression cassette can contain a marker gene which confers a selectable phenotype on the onion cells. For example, the marker may encode biocide resistance, particularly antibiotic resistance, such as resistance to kanamycin, G418, bleomycin, hygromycin, or herbicide resistance, such as resistance to glyphosate or chlorosulforon.

An expression cassette containing the heterologous gene can be introduced into onion using the Ti plasmid of *Agrobacterium tumefaciens* or the Ri plasmid of *Agrobacterium rhizogenes*. The Ti or Ri plasmid is transmitted to plant cells on infection by *Agrobacterium* and is stably integrated into the plant genome. Ti and Ri plasmids contain two regions essential for the production of transformed cells. One of these, named transfer DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid. The transferred DNA region can be increased in size by the insertion of heterologous DNA without its ability to be transferred being affected. Thus, a modified Ti or Ri plasmid, in which the disease-causing genes have been deleted, can be used as a vector for the transfer of the gene constructs of this invention into an appropriate plant cell. Construction of recombinant Ti and Ri plasmids in general follows methods typically used to introduce additional DNA into the more common bacterial vectors, such as pBR322. Additional use can be made of accessory genetic elements sometimes found with the native plasmids and sometimes constructed from foreign sequences. These may include, but are not limited to, "shuttle vectors" and structural genes for antibiotic resistance as a selection factor.

The nodular embryogenic callus material prepared as described above is then contacted with the Ti or Ri plasmid of *Agrobacterium tumefaciens* or *Agrobacterium rhizogenes* which contains the expression cassette with the heterologous gene. After the embryogenic callus material is contacted with the *Agrobacterium*, it is then incubated for about two (2) to about four (4) days at a temperature of about 20° C. to about 25° C. in the dark. After the incubation period, the *Agrobacterium* is removed or disinfected such as by scraping callus tissue into a dish with wash media, such as the wash medium described in Table B, agitating it and then removing the wash medium.

After removal of the *Agrobacterium*, the washed embryogenic callus material is transferred to a selection medium, such as the selection medium described in Table A as media number four (#4). Other selection media, which are well known in the art, such as media containing the antibiotic kanamycin, can also be used. The callus cultures are grown under Cool White fluorescent light for about 14 to about 18 hours per day at a temperature between about 25° C. to about 30° C.

After about thirty (30) days, the callus is subcultured onto a second higher selection media, such as the selection medium described in Table A as media number five (#5), for all following transfers. Selection transfers are done every four (4) weeks per subculture.

Any remaining callus which is living and is producing embryos or plants is then transferred to the rooting media in 0.05 mM glyphosate which is described in Table A as media #6 for final regeneration. Other rooting media which are well known in the art can also be used. The regenerating shoots are grown under Cool White fluorescent light for about 14 to about 18 hours per day at a temperature between about 25° C. to about 30° C. Regenerated and rooted shoots are then transplanted into pots filled with soil under high light intensity, such as 1000 foot candles, and at near 100% relative humidity, such as by covering the pots with plastic.

The shoots are allowed to continue to grow and develop into transformed *Allium* plants which contain the heterologous gene. Transformed plants containing the heterologous gene described herein can be identified using techniques known in the art such as Northern or Southern Blotting or polymerase chain reaction, By way of example and not of limitation, examples of the present invention will now be given.

Example 1

Materials and Methods a. Callus initiation—Immature embryos from onion, specifically, *Allium cepa* or *Allium fistulosum*, were isolated under a dissecting microscope from approximately 14 day post pollinated flowers. Flower heads can be shipped overnight from various breeding stations around the US, refrigerated and used as explant source for a period of about one (1) to about two (2) weeks. Individual flower buds were removed from the umbel and placed in a 15 ml screw cap centrifuge tube. Full strength Clorox plus 0.5% Tween 20 were added to the tube and mixed every 2-3 minutes for 15 minutes. Clorox was removed and buds were washed 4 times with sterile Reverse Osmosis (RO) water. Embryos were isolated by placing the bud on a sterile Petri dish under a 40× dissecting microscope with the flower base facing up. Using a #11 scalpel, the base of the flower was cut to the point of just removing the bottom of the pollinated seed. The seed coat is black and the endosperm is milky to doughy in consistency. The embryos can be squeezed out of the incision on the bottom of the seed with forceps pressure on the top third of the flower bud. However, this procedure may not be successful with older flowers where the endosperm is harder and the embryo is larger. Under these conditions, the seed is extracted from the flower bud for individual embryo excision. These embryos are excised by slicing down the seed coat on the side where the embryo is located. The embryo is extracted from the seed through the incision. Embryos are lifted from the plate on the scapel tip and placed on callus initiation medium (described in Table A as medium #1). Embryos range in size from 1-5 mm.

Plates 60×20 mm containing 40 ml media can hold up to 25 embryos. A nodular callus forms on the embryo after about 2 to about 4 months. Callus is maintained by subculture for about 3 to about 4 weeks on callus medium #1 shown in Table A. Callus tissue is grown at about 28° C. in the dark. Selection of nodular embryogenic tissue is important at each subculture. Removal of brown or smooth consistency tissue, tissue with anthocyanin or sticky exudates promotes development of embryogenic callus.

b. Callus regeneration—Nodular selected tissue is transferred to 60×20 mm plates containing 40 ml of regeneration medium (described in Table A as medium #2). Cultures are placed under 100 foot candles of Cool White fluorescent light for 16 hours per day at a temperature of about 28° C. Tissue is subcultured at about 3 to about 4 weeks, with embryo regeneration seen at 6-8 weeks.

c. Callus transformation—*Agrobacterium tumefaciens* cultures are initiated from streaked plates of freezer stock. Two loops of plate stock or 100 ul of freezer stock are placed in 5 ml YEP medium (described in Table B) containing appropriate antibiotics in a 25×150 mm tube and placed on a roller drum in room light. Overnight cultures are subcultured by adding 5 ml of the overnight culture to 50 ml of AB medium (described in Table B) with antibiotics and grown in the dark overnight at 28° C. on a gyratory shaker. The next day identified regenerable callus is placed on glass filter paper over co-culture medium (described in Table A as medium #3). Callus tissue is placed on the filter paper at a moderate density. Only nodular tissue is selected for transformation. Overnight *Agrobacterium* cultures are adjusted to an optical density (OD) of from about 0.1-0.4, preferably 0.4, at 660 nm with dilution medium (Table B). Diluted cultures are drawn into a plastic sterile transfer pipette. Callus tissue is dabbed with the end of the pipette so a small amount of solution covers the callus tissue. Each callus piece in the plate is touched. The plates are sealed with Parafilm, placed in a black plastic box and incubated at 23° C. for 3 days. On day three, *Agrobacterium* is removed by scraping tissue into a 60×20 mm plate containing 10 ml of wash medium as described in Table B. Tissue is agitated with a transfer pipette followed by removal of the wash. Tissue is scraped into 40 ml selection media (described in Table A as medium #4) in a 60×20 mm Petri dish and sealed with Parafilm. Cultures are grown under 100 foot candles Cool White florescent light for 16 hr/day. After one month, callus is subcultured into a second selection media (described in Table A as medium #5) for 2 transfers and back to selection media #4 (described in Table A) for 1 transfer. Any living callus is transferred to medium #2 (described in Table A) without selection for final regeneration. Regenerating embryos are placed on 50 ml rooting medium (described in Table A as medium #6) in Magenta containers and grown under similar light conditions.

Example 2

Specific Experiments

Experiment 212. Callus material used in this experiment was initiated from immature embryos from proprietary *Allium cepa* breeding material owned by Seminis Vegetable Seeds, Inc. Pollinated flowers were sent from Las Cruses, New Mexico to Woodland, Calif. and immature embryos were isolated, using the procedures described in Example 1a from 11 proprietary *Allium cepa* lines. Callus, recently subcultured for seventeen days, from the proprietary *Allium cepa* lines 197, 195, 193 and 248 were cocultured on medium #3 (described in Table A) for three days with disarmed *Agrobacterium* strain ABI containing Monsanto CP4 construct pMON10147 (Monsanto Company, St. Louis, Mo.). The construct pMON10147 contains the enhanced 35S promoter from figwort mosaic virus (which is disclosed in U.S. Pat. No. 5,633,435, hereby incorporated by reference), the leader sequence from the Petunia heat shock protein 70 (HPS70) (disclosed in Winter J., et al., *Mol. Genet.* 211:315-319 (1988), hereby incorporated by reference), the chloroplast transit peptide sequence (CTP2) of the 5-enolpyruvylshikimate-3-phosphate synthase gene (EPSPS) from *Arabidopsis thaliana* which is also disclosed in U.S. Pat. No. 5,633,435, the "modified" EPSPS gene from *Agrobacterium* sp strain CP4 which is disclosed in U.S. Pat. No. 5,633,435 and the 3' region from the small subunit of ribulose-1,5-bisphosphate gene from *Pisum sativum* (E9) which is also disclosed in Coruzzi, G., et al., *EMBO J.* 3:1671 (1984) and Morelli, G., et al., *Nature*, 315:200-204 (1985), hereby incorporated by reference.

The construct also contains the 35S promoter from cauliflower mosaic virus (CaMV), the chloroplast transit peptide sequence of the small subunit 1a (SSU1a) gene from *Arabidopsis thaliana* (disclosed in Timko M P., Herdies L., Alameida E., Cashmore A R., Leemans J. & Krebbers E. (1988) Genetic engineering of nuclear-encoding components of the photosynthetic apparatus of *Arabodopsis*. In The impact of chemistry on biotechnology—a multidisiplinary discussion—(Phillips M., Schoemaker S. P., Middlekauff D. & Ottenbrite R. M. eds) ACS Books, Washington DC, pp. 279-295), herein incorporated by reference), the modified glyphosate oxidoreductase gene (GOXsyn) from *Achromobacter* sp. (which is also disclosed in U.S. Pat. No. 5,633,435) and the 3' region of the nopaline synthase gene (nos) from *Agrobacterium tumafaciens* T-DNA.

a. The binary ABI strain contains the disarmed (lacking the T-DNA phytohormones) pTiC58 plasmid pMP9ORK (Koncz, C. and Schell, J., 1986. "The Promoter of TL-DNA Gene 5 Controls the Tissue-Specific Expression of Chimeric Genes Carried by a Novel Type of *Agrobacterium* Binary Vector," *Mol. Gen. Genet.* 204: 383-396.), in a chloramphenicol resistant derivative of the *Agrobacterium tumefaciens* strain A208. The pMP9ORK Ti plasmid was engineered to provide the gene functions required for autonomous replication of the plasmid vector after conjugation into the ABI strain. It also provides the vir functions needed for transfer of the T-DNA into the plant cell.

Callus was transferred, after washing, to callus medium #2 (described in Table A) without selection and grown in the dark. Callus was subcultured after 4 weeks on regeneration medium #4 (described in Table A) with 0.1 mM glyphosate and moved to the light. Callus was cultured for 3 additional months, with monthly transfers on 0.1 mM glyphosate selection (on medium #4 described in Table A) totaling 4 months. Callus line 248 initially established on Gelrite solidified medium (which is medium #1 described in Table A) produced 2 callus lines after glyphosate selection. These lines were subcultured on regeneration medium #2 (described in Table A) without selection. After 2 months, plants were placed on rooting medium #6 (described in Table A).

b. Experiment 268. This experiment employed additional immature embryos obtained from the proprietary line described above in Example 2a. These embryos underwent callus transformation as described above in Example 1c. Moreover, additional callus material used in this experiment was initiated from immature onion flower tissue which originated from proprietary onion line of Seminis Vegetable Seeds, Inc. which is derived from a cross of *Allium fistulosum×Allium cepa*. Amphidiploid plant materials of the original *Allium fistulosum×Allium cepa* cross (after colchicine-induced chromosome doubling) was released by Gil McCollum at the U.S.D.A, Beltsville (Notice of Release of Onion Germplasm f-c 8434, 8492, 8497 and 8615, USDA, ARS, Feb. 2, 1988).

To initiate callus from flowers, unopened umbels were cut and sterilized in 20% Clorox for 5 minutes then rinsed with sterile water. Whole flower buds were excised from the umbels and cultured 20 per plate on callus initiation medium #1 (described in Table A). Callus was maintained with monthly subcultures. Eleven flower callus lines were tested for regeneration and found not to regenerate at the frequency of immature embryo derived material. Flower callus line 290011, identified as a regenerating line, was used in experiment 268 along with 16 other embryo derived or flower derived callus lines. Callus was 15 days into its most recent subculture. Callus was cocultured for 3 days with ABI bacteria containing the Monsanto CP4 construct pMON45312 (Monsanto Company, St. Louis, Mo.). Construct pMON45312 contains the enhanced 35S promoter from figwort mosaic virus (FMV) (which is disclosed in U.S. Pat. No. 5,633,435, hereby incorporated by reference), the chloroplast transit peptide sequence (CTP2) of the 5-enolpyruvylshikimate-3-phosphate synthase gene (EPSPS) from *Arabidopsis thaliana* (which is also disclosed in U.S. Pat. No. 5,633,435), the leader sequence from the soybean heat shock protein (native 17.9) (disclosed in Arfchke, E., et al., J. Molec. Bio. 199:549-557 (1988), herein incorporated by reference), the "modified" EPSPS gene from *Agrobacterium* sp. strain CP4 (which is also disclosed in U.S. Pat. No. 5,633,435), and the 3' region from the small subunit of ribulose-1,5-bisphosphate gene from *Pisum sativum* (E9) which is also disclosed in Coruzzi, G., et al., *EMBO J.* 3:1671 (1984) and Morelli, G., et al., *Nature,* 315:200-204 (1985), hereby incorporated by reference.

The ABI binary *Agrobacterium* strain pTiC58 contains the disarmed (i.e. lacking the T-DNA phytohormone genes) plasmid pMP9ORK (Koncz, C. and Schell, J., 1986. "The Promoter of TL-DNA Gene 5 Controls the Tissue-Specific Expression of Chimeric Genes Carried by a Novel Type of *Agrobacterium* Binary Vector." *Mol. Gen. Genet.* 204: 383-396), in a chloramphenicol resistant derivative of the *Agrobacterium tumefaciens* strain A208. The pMP9ORK Ti plasmid was engineered to provide the gene functions required for autonomous replication of the plasmid vector after conjugation into the ABI strain.

Tissue was induced after washing on regeneration medium #4 (described in Table A) containing 0.05 mM glyphosate and grown in the light. After one month, callus was moved to regeneration media #5 (described in Table A) containing 0.1 mM glyphosate for 2 transfers. Callus was transferred back to 0.05 mM glyphosate regeneration media #4 (described in Table A) for one month. Selected green callus areas were placed on regeneration media #2 (described in Table A) without selection for 2 months. Developing embryos were transferred to elongation rooting medium #6.

Example 3

Discussion

The choice of tissue for transformation in onion or any plant culture system is critical for successful production of transgenic plants. Experiment 212 used immature embryo derived callus of a proprietary *Allium cepa* line. Two selected callus lines which were transformed were regenerated from this experiment aided by the use of a regenerating embryogenic callus line as the initial tissue source.

Immature flowers may also be used as a callus source. Experiment 268 discloses using onion flowers as callus source, however, the initial regeneration screen showed poor regeneration in flower derived callus. The regenerating flower tissue used in Experiment 268 came from a proprietary line which was a *Allium fistulosum×Allium cepa* cross that was doubled to become tetraploid. It appeared to be very vigorous in culture and was one of the only flower derived lines that regenerated.

Experiments 212 varies from 268 by selection procedure although both produced transgenic callus lines. Experiment 212 callus was placed on a callus medium without selection and grown the dark. After 1 month, callus was moved to the light and selected on 0.1 mM glyphosate for 4 months. Experiment 268 was directly selected on 0.05 mM glyphosate on a regenerating medium in the light followed by 2 months selection on 0.1 mM glyphosate and a final selection on 0.05 mm glyphosate. Experiment 268 produced more lines, however, different genotypes were used.

Delay of selection is used in soybean glyphosate transformation and should be tested further in the onion procedure, however, selection immediately after coculture, as in experiment 268, produced transgenic lines. The reduction of glyphosate selection was done in experiment 268 due to the fact that glyphosate accumulates in tissue and may overwhelm any engineered plant resistance. This is also why regeneration is done without glyphosate selective pressure.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made to the composition, operation and arrangement of the method of the present invention described herein without departing from the concept and scope of the invention as defined in the following claims.

TABLE A

| Onion Media | Callus #1 | Regeneration #2 | Coculture #3 | Selection #4 | Selection #5 | Rooting #6 |
|---|---|---|---|---|---|---|
| MS Salt | 4.3 g/l | 4.3 g/l | 4.3 g/l | 4.3 g/l | 4.3 g/l | 4.3 g/l |
| B-5 Vitamins | 1 ml/l | 1 ml/l | 1 ml/l | 1 ml/l | 1 ml/l | 1 ml/l |
| Sucrose | 30 g/l | 30 g/l | 30 g/l | 30 g/l | 30 g/l | 30 g/l |
| Picloram | 1 mg/l | | | | | |
| BA | 0.9 mg/l | 1 mg/l | 1 mg/l | 1 mg/l | 1 mg/l | |
| Proline | | 2.5 g/l | 2.5 g/l | 2.5 g/l | 2.5 g/l | |
| $NaH_2PO_4$ | | | | | | 170 mg/l |
| Casein | | | | | | 1 g/l |
| Kinetin | | | | | | 1 mg/l |
| Acetosyringone | | | 40 mg/l | | | |
| Carbenicillin | | | | 500 mg/l | 500 mg/l | |
| Cefotaxime | | | | 400 mg/l | 400 mg/l | |
| Glyphosate | | | | 0.05 mM | 0.1 mM | 0.05 mM |
| Agar // or | 7 g/l | 7 g/l | 7 g/l | 7 g/l | 7 g/l | 6.2 g/l |
| Phytogel | 2.5 g/l | | | | | |
| pH | 5.7 | 5.7 | 5.7 | 5.7 | 5.7 | 5.8 |

TABLE B

| YEP Medium | |
|---|---|
| Peptone | 10 g/l |
| Yeast extract | 10 g/l |
| NaCl | 5 g/l |
| AB Medium | |
| Buffer: 20× Final Volume = | 500 ml |
| $K_2HPO_4 \cdot 3H_2O$ | 39.33 g |
| $NaH_2PO_4 \cdot H_2O$ | 11.5 g |
| Filter Sterilize and refrigerate | |
| Salts: 20× Final Volume = | 500 ml |
| $NH_4Cl$ | 10 g |
| $MgSO_4 \cdot 7H_2O$ | 12.5 g |
| KCl | 1.5 g |
| $CaCl_2$ | 0.1 g |
| $FeSO_4$ | 25 mg |
| Filter Sterilize and refrigerate | |
| Glucose - | |
| 50 g/500 ml | |
| Dilution Medium - | |
| 1/10 MSO + 1.0 mg/l BA + 2.5 g/l proline | |
| 200 uM Acetosyringone | |
| 1 mM galacturonic acid | |
| 20 mM MES (2-[N-morpholino]ethanesulfonic acid) | |
| pH 5.4 | |
| Wash | |
| MSO (MS medium plus minimal organics) | |
| 500 ug/l Carbenicillin | |
| 400 ug/l Cefotaxime | |

What is claimed is:

1. A method of transforming an amphidiploid *Allium cepa×Allium fistulosum* plant with a heterologous gene comprising;
   a. contacting amphidiploid embryogenic callus material from an amphidiploid *Allium cepa×Allium fistulosum* plant with a bacterium belonging to the genus *Agrobacterium* which contains a heterologous gene comprising a selectable marker gene; and
   b. obtaining a transformed amphidiploid *Allium cepa×Allium fistulosum* embryogenic callus under selective conditions.

2. The method of claim 1, further comprising growing said amphidiploid embryogenic callus material into a plant.

3. The method of claim 2, further comprising crossing said transformed amphidiploid *Allium cepa×Allium fistulosum* plant with an *Allium cepa* or *Allium fistulosum* plant.

4. The method of claim 1, wherein said bacterium belonging to the genus *Agrobacterium* is *Agrobacterium rhizogenes* or *Agrobacterium tumefaciens*.

5. The method of claim 1, wherein said bacterium belonging to the genus *Agrobacterium* contains a Ti plasmid or a Ri plasmid.

6. The method of claim 1, wherein said heterologous gene confers biocide resistance.

7. The method of claim 1, wherein said biocide resistance is selected from group consisting of glyphosate resistance, chlorosulforon resistance, kanamycin resistance, G418 resistance, bleomycin resistance, and hygromycin resistance.

8. The method of claim 7, wherein said biocide resistance is glyphosate resistance.

9. The method of claim 1, wherein said heterologous gene is the 5-enolpyruvylshikimate-3-phosphate synthase (ESPS) gene.

10. The method of claim 1, wherein said heterologous gene is a modified ESPS gene.

11. An amphidiploid *Allium cepa×Allium fistulosum* embryogenic callus, plant or plant tissue, each having a stably integrated heterologous gene, prepared by a method comprising: contacting an embryogenic callus from a plant of an amphidiploid *Allium cepa×Allium fistulosum* with a bacterium belonging to the genus *Agrobacterium* which contains a DNA of interest from a heterologous gene, and obtaining a transformed amphidiploid *Allium cepa×Allium fistulosum* embryogenic callus under selective conditions, wherein the stably integrated heterologous gene confers biocide resistance.

12. The amphidiploid *Allium cepa×Allium fistulosum* embryogenic Callus, plant or plant tissue of claim 11, that is a plant.

13. The amphidiploid *Allium cepa×Allium fistulosum* embryogenic callus, plant or plant tissue of claim 11, wherein said plant or plant tissue is a seed.

14. The amphidiploid embryogenic callus, plant or plant tissue of claim 11, wherein said bacterium belonging to the genus *Agrobacterium* is *Agrobacterium rhizogenes* or *Agrobacterium tumefaciens*.

15. The amphidiploid embryogenic callus, plant or plant tissue of claim 11, wherein said bacterium belonging to the genus *Agrobacterium* contains a Ti plasmid or a Ri plasmid.

16. The amphidiploid embryogenic callus, plant or plant tissue of claim 11, wherein said biocide resistance is selected from the group consisting of glyphosate resistance, chlorosulforon resistance, kanamycin resistance, G418 resistance, bleomycin resistance, and hygromycin resistance.

17. The amphidiploid embryogenic callus, plant or plant tissue of claim 16, wherein said biocide resistance is glyphosate resistance.

18. An amphidiploid *Allium cepa×Allium fistulosum* embryogenic callus, plant or plant tissue, each comprising a stably integrated heterologous gene, prepared by a method comprising:
   a. culturing immature embryos or flower buds from a plant of an amphidiploid *Allium cepa×Allium fistulosum* on an initiation medium for a period of from 2 to 6 months until an embryogenic callus forms on the embryos or flower buds;
   b. transferring the embryogenic callus to a coculture medium and contacting the embryogenic callus with a suspension of *Agrobacterium rhizogenes* or *Agrobacterium tumefaciens* containing a DNA of interest from a heterologous selectable marker gene; and
   c. obtaining a transformed amphidiploid *Allium cepa×Allium fistulosum* embryogenic callus under selective conditions;
   wherein the stably integrated heterologous gene confers biocide resistance.

19. The amphidiploid embryogenic callus, plant or plant tissue of claim 18, that is a plant.

20. The amphidiploid embryogenic callus, plant or plant tissue of claim 18, wherein said plant or plant tissue is a seed.

21. The amphidiploid embryogenic callus, plant or plant tissue of claim 18, wherein said bacterium belonging to the genus *Agrobacterium* is *Agrobacterium tumefaciens*.

22. The amphidiploid embryogenic callus, plant or plant tissue of claim 18, wherein said bacterium belonging to the genus *Agrobacterium* is *Agrobacterium rhizogenes*.

23. The amphidiploid embryogenic callus, plant or plant tissue of claim 18, wherein said bacterium belonging to the genus *Agrobacterium* contains a Ti plasmid or a Ri plasmid.

24. The amphidiploid embryogenic callus, plant or plant tissue of claim 18, wherein said resistance is selected from the group consisting of herbicide resistance and antibiotic resistance.

25. The amphidiploid embryogenic callus, plant or plant tissue of claim 24, wherein said herbicide resistance is glyphosate resistance or chlorosulforon resistance.

26. The amphidiploid embryogenic callus, plant or plant tissue of claim 25, wherein said herbicide resistance is glyphosate resistance.

27. The amphidiploid embryogenic callus, plant or plant tissue of claim 24, wherein said antibiotic resistance is selected from the group consisting of kanamycin resistance, G418 resistance, bleomycin resistance, and hygromycin resistance.

* * * * *